United States Patent
Kilsgaard et al.

(10) Patent No.: US 10,441,223 B2
(45) Date of Patent: Oct. 15, 2019

(54) ELECTRODE AND LEAKAGE CURRENT TESTING IN AN EEG MONITOR WITH AN IMPLANTABLE PART

(71) Applicant: Widex A/S, Lynge (DK)

(72) Inventors: Soren Kilsgaard, Smorum (DK); Morten Holm Jensen, Farum (DK)

(73) Assignee: T&W Engineering A/S, Lynge (DK)

( * ) Notice: Subject to any disclaimer, the term of this patent is extended or adjusted under 35 U.S.C. 154(b) by 1071 days.

(21) Appl. No.: 14/831,340

(22) Filed: Aug. 20, 2015

(65) Prior Publication Data
US 2015/0351654 A1 Dec. 10, 2015

Related U.S. Application Data (63) Continuation-in-part of application No. PCT/EP2013/053886, filed on Feb. 27, 2013.

(51) Int. Cl.
*A61B 5/00* (2006.01)
*A61B 5/04* (2006.01)
*A61B 5/0478* (2006.01)

(52) U.S. Cl.
CPC .......... *A61B 5/7221* (2013.01); *A61B 5/0006* (2013.01); *A61B 5/0031* (2013.01);
(Continued)

(58) Field of Classification Search
CPC ... A61B 5/0476; A61B 5/0478; A61B 5/6803; A61B 5/6814; A61B 5/6815;
(Continued)

(56) References Cited

U.S. PATENT DOCUMENTS 3,859,988 A * 1/1975 Lencioni, Jr. ........ A61B 5/0424
324/500
4,417,590 A 11/1983 Smith et al.
(Continued)

FOREIGN PATENT DOCUMENTS

EP 0354958 A1 2/1990
WO 2006/047874 A1 5/2006
(Continued)

OTHER PUBLICATIONS

International Search Report and Written Opinion of the International Searching Authority for PCT/EP2013/053886 dated Nov. 4, 2013.

*Primary Examiner* — Eun Hwa Kim
(74) *Attorney, Agent, or Firm* — Sughrue Mion, PLLC (57) ABSTRACT

A personal wearable EEG monitor comprising an implantable electrode part with at least two electrodes (2,3) for measuring an EEG signal of a person. The electrode part comprises an electronic circuit arranged in a housing (1) with each electrode arranged external to the housing. The electrode part comprises a testing circuit for testing functionality of the electrode part. The testing circuit comprises a capacitor (9) coupled in serial connection to at least one of the electrodes, and a test signal generator for providing a test signal. The EEG monitor is adapted for analyzing the signal resulting from the signal generator for identification of faults in the electrode part. The invention further provides a method for detecting a leak current in an implanted EEG monitor part.

13 Claims, 6 Drawing Sheets

(52) U.S. Cl.
CPC ...... *A61B 5/04004* (2013.01); *A61B 5/04017* (2013.01); *A61B 5/0478* (2013.01); *A61B 5/6846* (2013.01); *A61B 5/7203* (2013.01); *A61B 5/72* (2013.01); *A61B 2560/0266* (2013.01)

(58) Field of Classification Search
CPC ... A61B 5/6868; A61B 5/7207; A61B 5/7217; A61B 5/7221; A61B 5/0031; A61B 5/0006; A61B 5/0417; A61B 5/04004
See application file for complete search history.

(56) References Cited

U.S. PATENT DOCUMENTS

| | | | |
|---|---|---|---|
| 5,814,996 | A | 9/1998 | Winter |
| 6,313,741 | B1 * | 11/2001 | Glabe ................... B60T 8/885 |
| | | | 303/122 |
| 6,807,438 | B1 | 10/2004 | Brun Del Re |
| 2006/0122529 | A1 | 6/2006 | Tsau |
| 2011/0066020 | A1 | 3/2011 | Svojansky |
| 2011/0137371 | A1 | 6/2011 | Giftakis et al. |

FOREIGN PATENT DOCUMENTS

| | | |
|---|---|---|
| WO | 2006/066577 A1 | 6/2006 |
| WO | 2009/082783 A1 | 7/2009 |
| WO | 2010/124738 A1 | 11/2010 |

* cited by examiner

ELECTRODE AND LEAKAGE CURRENT TESTING IN AN EEG MONITOR WITH AN IMPLANTABLE PART

RELATED APPLICATIONS

The present application is a continuation-in-part of application PCT/EP2013053886, filed on 27 Feb. 2013, in Europe, and published as WO2014131438 A1.

BACKGROUND OF THE INVENTION

1. Field of the Invention

The present invention relates to EEG monitors. The invention, in particular relates to EEG monitors of types that can be continuously carried by a person being monitored. The invention further relates to a personal wearable EEG monitor comprising an implantable electrode part with at least two electrodes for measuring an EEG signal of a person, said electrode part comprising an electronic circuit arranged in a housing with each electrode arranged external to said housing.

EEG is the commonly used abbreviation for Electro Encephalo-Graphy, which is generally speaking a method of electrically monitoring brain activity of a person. Systems for monitoring EEGs have been known for many years. However with the general technological development, EEG monitoring systems, that may be carried or worn continuously by a person to be monitored have been devised.

It is known to measure EEG by placing electrodes on the scalp of a person, and to record and analyse the EEG signal for various diagnostic purposes.

2. The Prior Art

A system for such a use is known from WO-A1-2006/047874, which describes measurement of brain waves by use of electrodes placed in connection with at least one of the ears of the subject, i.e. placed on an outer ear part or placed in the ear canal. The measurements are used particularly for detecting the onset of an epileptic seizure. WO-A1-2006/047874 also describes the use of EEG electrodes in pairs as detection and reference electrodes respectively.

EEG monitors may also be applied for surveillance of persons having diabetes, where low blood sugar levels may cause hypoglycaemic attacks. Hypoglycaemic attacks may lead to unconsciousness. A system for surveillance of the EEG signal where changes may indicate an imminent hypoglycaemic attack is disclosed in WO-A-2006/066577. This discloses an implanted subcutaneous system. EEG monitors may also be applied for other purposes, such as detecting imminent seizures of epilepsy.

In EEG monitors with implanted electrodes there will also be implanted electronics for sampling the EEG signal, and either transmitting the signal to a non-implanted part, or processing the signal in the implanted part.

One problem in an implanted electrode part is that controlling that everything functions as planned might be difficult. There is a need to check if the electrodes are unbroken, e.g. that the electrical connection to the electrodes has not been interrupted. There is a need to check that no current leaks from the implant into the tissue, or to verify that any such leak is below a given threshold.

Any leak current flowing out from the electrodes shall be smaller than 0.1 µA. In single fault conditions, e.g. the DC blocking capacitor failing, the current shall be less than 1 µA.

The implant should thus measure if the leakage current is above 1 µA upon startup of the implanted electrode device.

Current running in the human body due to an implanted device, i.e. current flowing out from the electrodes, must not exceed acceptable limits. ISO 14708-1 Clause 16.2 states a limit of 1 µA. The analog frontend design should preferably be an AC-coupled (DC-blocking) amplifier ensuring that practically no currents run out of the electrodes under normal working conditions.

SUMMARY OF THE INVENTION

The present invention, in a first aspect, provides a personal wearable EEG monitor comprising an implantable electrode part with at least two electrodes adapted for measuring an EEG signal of a person, said electrode part comprising an electronic circuit arranged in a housing with each electrode arranged external to said housing, said electronic circuit being adapted for receiving an analogue EEG signal from said electrodes and being provided with an analogue to digital converter for converting the analogue EEG signal into a digital signal, said electrode part comprising a testing circuit for testing for faults in said electrode part, wherein said testing circuit comprises a capacitor coupled in serial connection to at least one of said electrodes, and a test signal generator for providing a test signal, said test signal generator being adapted for being coupled between said electrodes and said electronic circuit during a testing period, wherein said EEG monitor is adapted for analyzing the signal resulting from said signal generator for identification of faults in the electrode part.

Examples of the testing for faults in the electrode part could be to test if there is leak current, if the electrodes are broken so that there is no connection, or if the capacitor is broken.

In an embodiment of the EEG monitor the test signal generator is arranged between the electrodes and the analogue to digital converter, and the EEG monitor is adapted for analyzing the analogue to digital converter input signal resulting from the signal generator for identification of faults in the electrode part.

In an embodiment of the EEG monitor the signal from the analogue to digital converter is transferred to a digital signal processing unit also arranged in the electrode part.

In an embodiment of the EEG monitor a resistor is arranged across the input of the analogue to digital converter. This enables measuring the impedance between electrode and tissue.

In an embodiment the EEG monitor is adapted for identifying a charging or discharging function at the analogue to digital converter input and thereby detecting a current leak.

The charging or discharging function will be from the charging or discharging of the capacitor.

In an embodiment of the EEG monitor the implantable electrode part comprises a coil for an inductive coupling to a non-implantable part, the inductive coupling being adapted for transfer of data and power.

In an embodiment of the EEG monitor the test signal generator provides a square wave test signal with frequency between 25 and 40 Hz.

The invention, in a second aspect, provides a method for detecting a leak current in an implanted EEG monitor part comprising an implantable electrode part with at least two electrodes adapted for measuring an EEG signal of a person, said electrode part comprising an electronic circuit arranged in a housing with each electrode arranged external to said housing, said electronic circuit being adapted for receiving an analogue EEG signal from said electrodes and being provided with an analogue to digital converter for converting the analogue EEG signal into a digital signal, said electrode part comprising a testing circuit for testing for faults in said electrode part, wherein said testing circuit comprising the steps of providing a test generator signal, subtracting the estimated test generator signal from the signal at the analogue to digital converter, low-pass filtering the resulting signal in order to suppress EEG and noise components, transforming the signal into a logarithmic domain, fitting the signal to a straight line, determining the interception with y-axis of the straight line, and determining if leak current is present.

In an embodiment of the method the low-pass filtered signal is downsampled in order to reduce the calculation complexity.

In an embodiment of the method the step of transforming the signal comprises taking the power of the signal or taking the absolute value of the signal and then taking the natural logarithm of the power signal or taking the natural logarithm of the absolute value of the signal.

It is known, e.g. from WO-A1-2010/124738, to have an EEG monitoring system comprising an implantable part and an external part. The implantable part, suitable for being subcutaneously positioned behind the ear of a person in need of EEG monitoring, comprises a subcutaneous EEG electrode having a plurality of active areas separated by isolators. The electrode is connected to an electronic circuit. The EEG electrode has at least two active areas. Often these active areas are simply referred to as electrodes. This is also done below. The electronic circuit preferably comprises an A/D converter, a data packet controller, a communications controller, and a voltage regulator. The electrode is connected to the input terminals of the A/D converter via electrode wires, the communications controller, if present, may be connected to a first communications coil, and the voltage regulator, if present, may be connected to a ceramic capacitor. The external part of the EEG monitoring system preferably comprises a controller which may be connected to a second communications coil, a battery for powering the controller, and possibly a loudspeaker for providing an acoustic signal, e.g. an alarm, in the event of a seizure coming up.

When in use, the external part of the EEG monitoring system may be placed behind the ear of a user for whom monitoring of an EEG signal is desired, and in the vicinity of the subcutaneously implantable part. The implantable part is often implanted right below the skin and slightly behind the ear of the user and positioned in such a way that a reliable, electrical EEG signal may be detected by the electrodes.

The electrodes pick up EEG signals as a varying electrical voltage potential and feeds the varying electrical voltage to the input terminals of the A/D converter via the electrode wires. The A/D converter converts the varying electrical voltage from the electrode into a digital signal and may present said digital signal to the data packet controller. The data packet controller preferably arranges the digital signal representing the electrical signal from the electrode into a stream of data packets according to a predetermined communications protocol, and feeds the resulting stream of data packets to the communications controller.

The communications controller is typically configured to alternate between two operational states. The first state of the communications controller preferably enables the electronic circuit to be energized electromagnetically by receiving energy from the second communications coil of the external part by the first communications coil. The electromagnetic energy received in the first communications coil may be transferred by the communications controller to the voltage regulator and stored briefly as a voltage charge in the ceramic capacitor. The electrical energy stored in the ceramic capacitor is then used as a power source for the electrical circuit in the implant.

The second state of the communications controller takes data packets representing the electrical EEG signals from the electrode from the data packet controller and converts them in the first communications coil into bursts of electromagnetic energy suitable for being received and detected by the second communications coil of the external part. The second communications coil may convert the received bursts of electromagnetic energy into an electrical signal suitable for being continuously decoded and analyzed by the controller.

Depending on the results of the analysis of the EEG signals, decisions may be taken by the controller to activate the loudspeaker sounding an alarm, e.g. when a predetermined medical condition is deemed to be present from the analysis of the EEG signals. This alarm may then alert a user to the medical condition, and allow him or her to take adequate steps to alleviate the medical condition, e.g. by taking a prescription drug or consulting medical personnel to ask for immediate advice or help, depending on the medical condition.

BRIEF DESCRIPTION OF THE DRAWINGS

Embodiments of the invention will now be explained in further detail with reference to the figures.

DETAILED DESCRIPTION OF THE INVENTION

Figure 1:
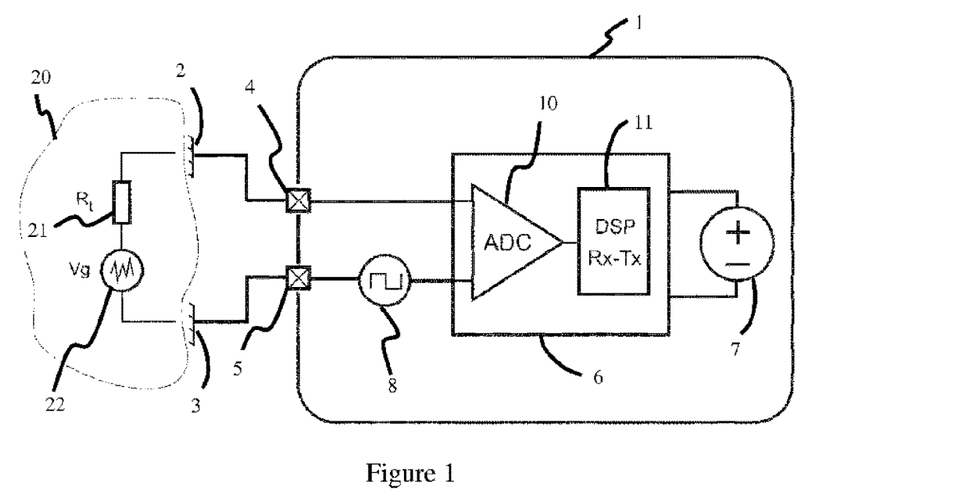
FIG. 1 illustrates an embodiment of an implantable part of an EEG monitor provided with a test generator.

FIG. 1 shows an implantable part of an EEG monitor, or simply an implant device, with a housing 1 and with implant terminals 4, 5 connected to the electrodes 2, 3, which are in direct contact with the tissue 20. There will be some contact impedance 21 denoted $R_t$ between the tissue and the electrodes. The EEG potential 22 denoted $V_g$ will be picked up by the electrodes 2, 3. The implant housing 1 will comprise an implant electronic module 6 having an analogue to digital converter (ADC) 10, for converting the analogue EEG signal into a digital signal, and a digital signal processing and microcontroller unit (DSP) 11.

The DSP 11 may prepare the EEG signal for transmission to an external non-implanted part of the EEG monitor, so that the further analysis of the EEG signal can be performed there. The DSP 11 may also perform the necessary analysis of the EEG signal in order to identify an imminent seizure or attack. The DSP 11 may also comprise a receiver and transmitter system (Rx-Tx) for communication with the surroundings.

The housing 1 of the implant device also comprises a power supply 7. This may be in the form of a battery, e.g. a rechargeable battery. Other types of voltage supply could be any type of power generating means, such as an inductive coupling between a coil in the implant and a non-implanted coil arranged outside the skin and geometrically aligned to maximize the transfer of power to the implanted coil. Typically, the receiver and transmitter system will also apply such an inductively coupled pair of coils for communication between the internal, i.e. implanted, and the external parts of the EEG monitor. Preferably, the same set of coils can thus be applied both for the transfer of power and for the transfer of data.

In FIG. 1 a test signal generator or voltage generator 8 is inserted between the implant terminal 5 and the ADC 10. This generator may supply a sine wave, a square wave or any other signal. The signal from the generator 8 is applied for determining if there is conductivity between the housing 1 for the implant and the electrodes. The frequency of the signal should preferably be within the bandwidth of the ADC.

The generator 8 could be inserted during start-up of the monitor or at predefined intervals.

Figure 2:
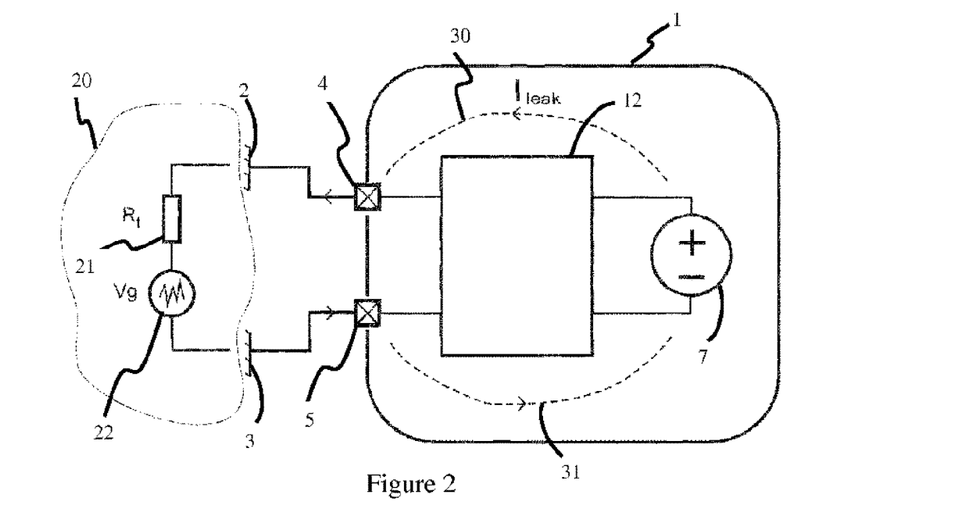
FIG. 2 illustrates an implantable part with two leak current routes.

FIG. 2 shows how possible leak currents may flow during monitoring of the EEG signal. The leak current will flow if there is any leak in the housing 1. Two possible leak paths 30, 31 exist.

In differential measurement both leak paths 30, 31 must be present before there is a risk that a DC current can go through tissue. The risk of having two leak paths should be small.

Figure 3:
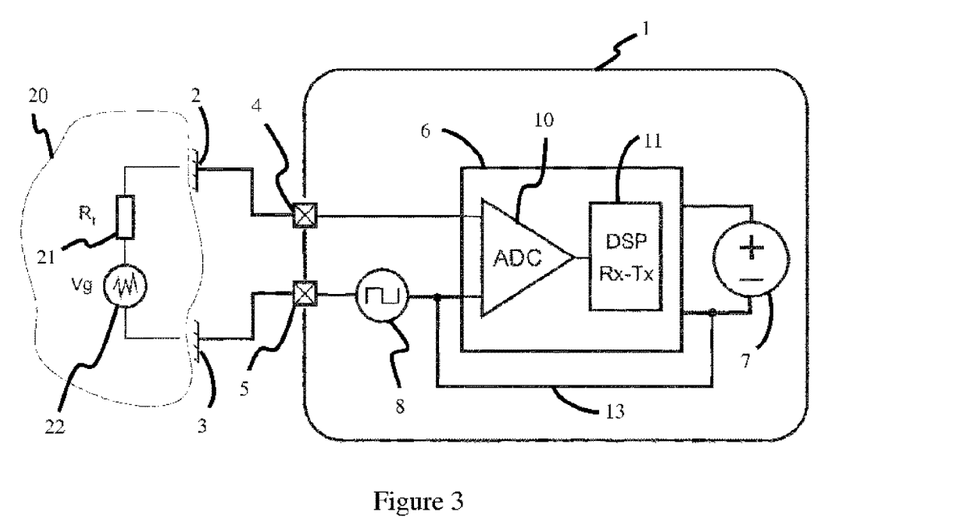
FIG. 3 illustrates the implantable part from FIG. 1 with the test generator grounded.

In single-ended measurements only one leak path is necessary in order to have a leak DC current go through tissue. The setup of the test voltage generator for this situation is shown in FIG. 3, where the signal generator 8 together with the lower input to the ADC 10 has been grounded by the connection 13. With this set-up there will be no leak current along the lower leak path 31 in FIG. 2.

With the set-up of the test generator 8 in FIG. 3 it will be possible to see if the electrodes are broken, i.e. if there is no connection through the electrodes.

Figure 4:
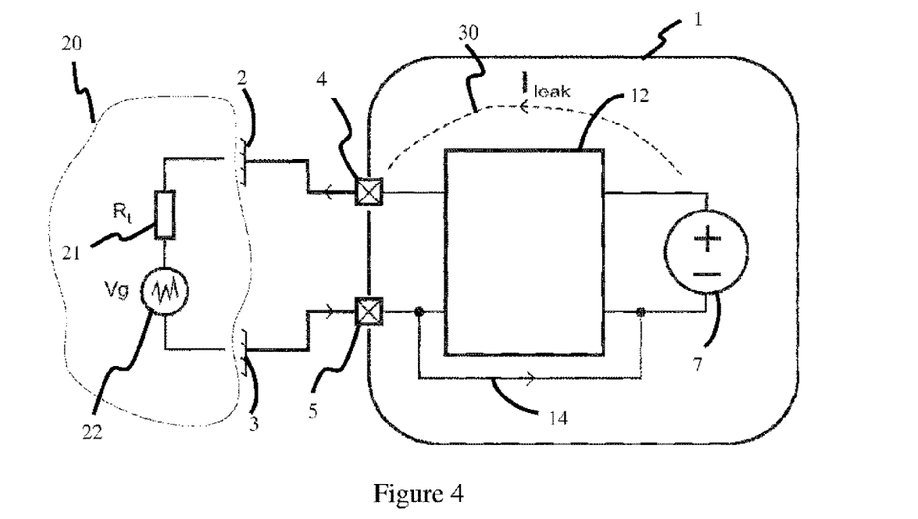
FIG. 4 illustrates the leak current route from the implantable part in FIG. 3.

FIG. 4 shows the possible leak path 30 to the implant terminal 4 for a single ended measuring system. This leak path may result in a leak current $I_{CL}$ through tissue. In the embodiment of FIG. 4 the terminal 5 is grounded. A leak path 14 to the lower implant terminal 5 will not result in current through the tissue surrounding the implant part.

Figure 5:
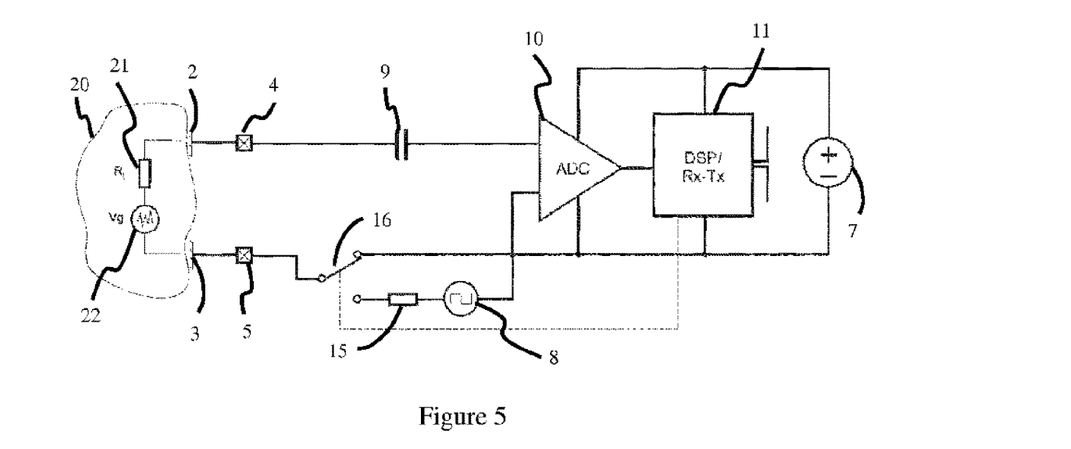
FIG. 5 illustrates the implantable part from FIG. 3 in more detail and with a capacitor between electrodes and analogue to digital converter (ADC).

In FIG. 5 the control of the test generator 8 is shown in the case of single-ended EEG measurement. A possible leak path here could be from the positive pole of the power supply 7 and to the implant terminal 4. The frequency of the generator 8 shall be in the range of the ADC 10, i.e. below half the sample rate of the ADC. The wave form of the generator 8 can for example be square or sine.

The switch 16 is controlled from the DSP unit 11. In the position of the switch 16 in FIG. 5 the test generator 8 is de-coupled or not active, and the implant will be in EEG monitoring mode. When the position of the switch 16 is changed to couple the test generator 8 into the circuit it is possible to measure if the electrode is broken and to measure if there is a leak current into the tissue surrounding the implant.

In order to test for a broken electrode in the test circuit in FIG. 5, the output signal of the ADC 10 could be band pass filtered (e.g. around 30 Hz) in order to remove EEG signal. If a signal originating from the generator 8 can be seen in the output from the band pass filter (which is part of the DSP 11) then the electrode is not broken. Otherwise the electrode might be broken.

In order to test for a leak current from the implant to the body tissue, the output of the ADC 10 could be low pass filtered, e.g. at a cutoff frequency at approximately 10 Hz. At the time t=0, e.g. when the implant is started up, the absolute value of the low pass filtered ADC output voltage is measured, and if this is greater than a preset threshold value (e.g. 1 mV), then there is a leak current through body tissue.

The circuit of FIG. 5 also comprises a capacitor 9 in serial connection between the ADC 10 input and an EEG electrode 2. This capacitor is applied for the leak current testing. At the same time the capacitor 9 offers protection against current leak, since it will block any DC component from the electronic circuit 12 from entering the electrodes. Also the capacitor may block a DC component of from the electrodes from entering the ADC 10.

Figure 6:
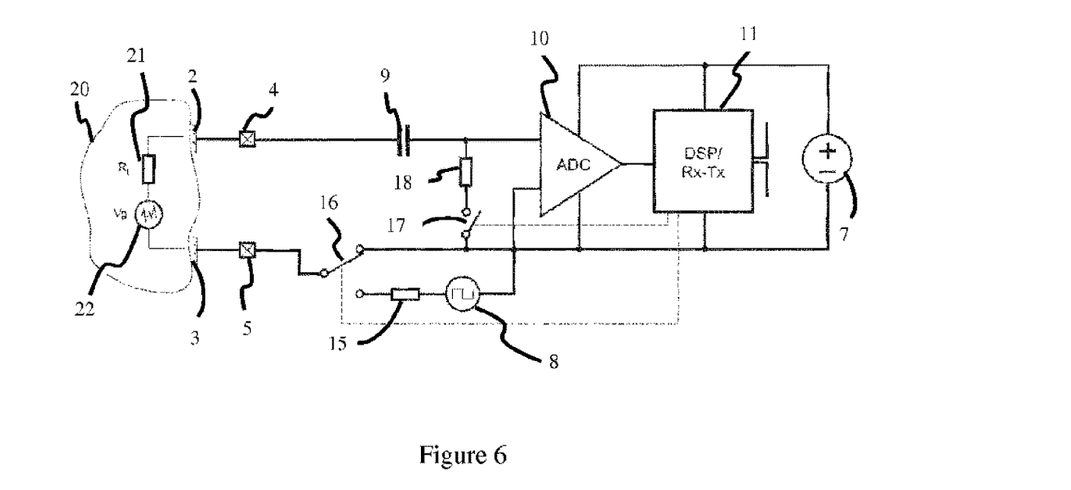
FIG. 6 illustrates the implantable part from FIG. 5 with a resistor on the ADC input.

In FIG. 6 a resistor 18 is arranged across the input of the ADC 10. This resistor is in serial connection with a switch 17 for switching the resistor 18 into the circuit. Switching the resistor 18 into the circuit is relevant when the test generator 8 is active. Then it is possible to estimate electrode impedance $R_t$ 21. The magnitude of the electrode impedance 21 is determined by how good the contact is between the tissue and the electrodes 2, 3.

Figure 7:
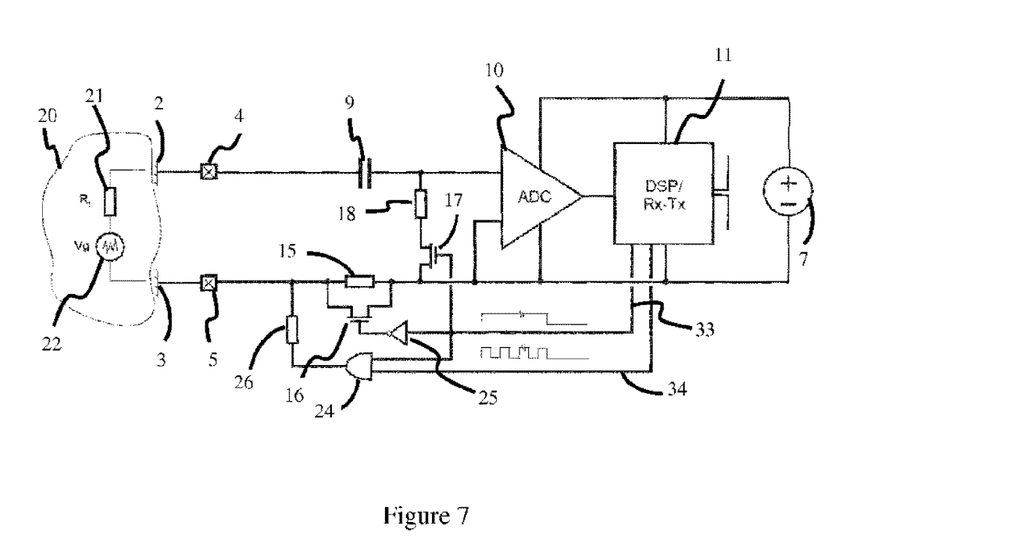
FIG. 7 illustrates the implantable part from FIG. 6 with a possible implementation of a test circuit shown.

FIG. 7 shows an example of how the test generator 8 and the two switches 16, 17 of FIG. 6 might be implemented. The test generator is implemented through an AND gate 24 and a resistor 26. The AND gate is controlled by one signal line 33 providing a control signal from the DSP 11 sending a "1" (i.e. being high) when the test generator 8 needs to be active, and by one signal line 34 providing the test signal, here in the form of a square waveform.

Both switches 16, 17 are implemented as transistors, which are also controlled by the signal line 33. The switch 16 is connected to the signal line 33 through a NOT gate 25 in order for this switch 16 to be open when the test is running. When the switch 16 is closed the resistor 15 is short-circuited. During testing the switch 17 receives a "1" or high through the signal line 33, and is thereby closed such that the resistor 18 is connected between the two input terminals of the ADC 10.

In the following an example of how a broken electrode could be detected is given.

Referring to FIG. 5, the ADC 10 input voltage $V_{ADC}$ is a high-pass filtered version of the sum of the EEG signal 22 and the signal from the test generator 8 assuming switch 16 is in lower position. In the present example test signal 8 is squared and has a frequency at 34.5 Hz and has an amplitude of about 1 mV. The test signal could e.g. be applied for the first second after the implanted device is powered up. Since EEG signals typically will have an amplitude of 10-100 µV and a frequency range of 0.5-20 Hz the test signal will be clearly distinct from the EEG signal. This can easily be detected by the following signal processing.

There are several methods to "detect" or "calculate" the 34.5 Hz signal at the ADC input. One method is to calculate the Discrete Fourier Transform (DFT) at 34.5 Hz. The numerical value of the DFT is then compared to a preset threshold, and if the DFT is above it, it is assumed that the electrode is intact.

Furthermore, from the output of ADC 10 it can be checked if the DC blocking capacitor 9 is intact. Normally there will be no DC contribution at the output of ADC 10 due to the high-pass filtering established by capacitor 9 and the input impedance of ADC 10. If for instance capacitor 9 goes from normal state to a shorted state, a DC contribution at the output of the ADC 10 will appear. This is due to the half-cell potential produced by the electrode in combination with body tissue. Such a DC can easily be detected by the following signal processing and can result in a warning or an alarm to the user. Otherwise, if the capacitor 9 blocks, no test signal or EEG signal will be seen at the output if the ADC 10. This again is easy to detect by the following signal processing and can result in a warning or an alarm to the user. This analysis is not necessarily depending on the test generator 8, and therefore, constant monitoring of the DC blocking capacitor condition is possible.

Reference is again made to FIG. 5, now with the existence of a current path from the positive terminal of power supply 7 to the wire that connects to terminal 4 or the terminal 4 itself. In case the power supply 7 is an inductive powered voltage supply, there will be no voltages or currents in the implant when the external power transmitting system is turned off. As a consequence no current leak will run either. At the time when an external power transmitting system is turned on, the implant device 1 starts to harvest energy from the magnetic field. At the same time a current starts to run into the electrode due to the current leakage path. The leakage current is denoted $I_{CL}$. If present, this current will generate a voltage over resistor 21 and resistor 15, assuming switch 16 is in lower position. The voltage at the output of ADC 10 which originates from the current leak is denoted $V_{CL}$ and has the form:

$$V_{CL} = \alpha \cdot e^{(-t/\tau)}$$

The time constant is $$\tau = C(R_t + R_g + R_{ADC}) \approx C \cdot R_{ADC}$$

The approximation holds when $R_{ADC}$ is much larger than $R_g$ and $R_t$. C is the capacitor 9, $R_g$ is the impedance 15 of the test generator 8, $R_t$ is the impedance 21 between tissue and electrode, and $R_{ADC}$ is the input impedance (not shown) of the ADC 10.

When starting up from an un-powered state the typical scenario will be that switch 16 is in the lower position. In this case α is given by $$\alpha = \frac{I_{CL}(R_t + R_g)R_{ADC}}{R_{ADC} + R_t + R_g} \approx I_{CL}(R_t + R_g)$$

When the test period has elapsed, switch 16 goes from the lower position to the upper and result in an α value and a time constant τ given by:

$$\alpha = \frac{(I_{CL} \cdot R_t - I_{CL}(R_g + R_t)) \cdot R_{ADC}}{R_{ADC} + R_t} = \frac{-I_{CL} \cdot R_g \cdot R_{ADC}}{R_{ADC} + R_t} \approx -I_{CL} \cdot R_g$$

$$\tau = C(R_t = R_{ADC}) \approx C \cdot R_{ADC}$$

$V_{CL}$ follows a charge function when the implant is turned on and a discharge function when the test period has elapsed.

Figure 8:
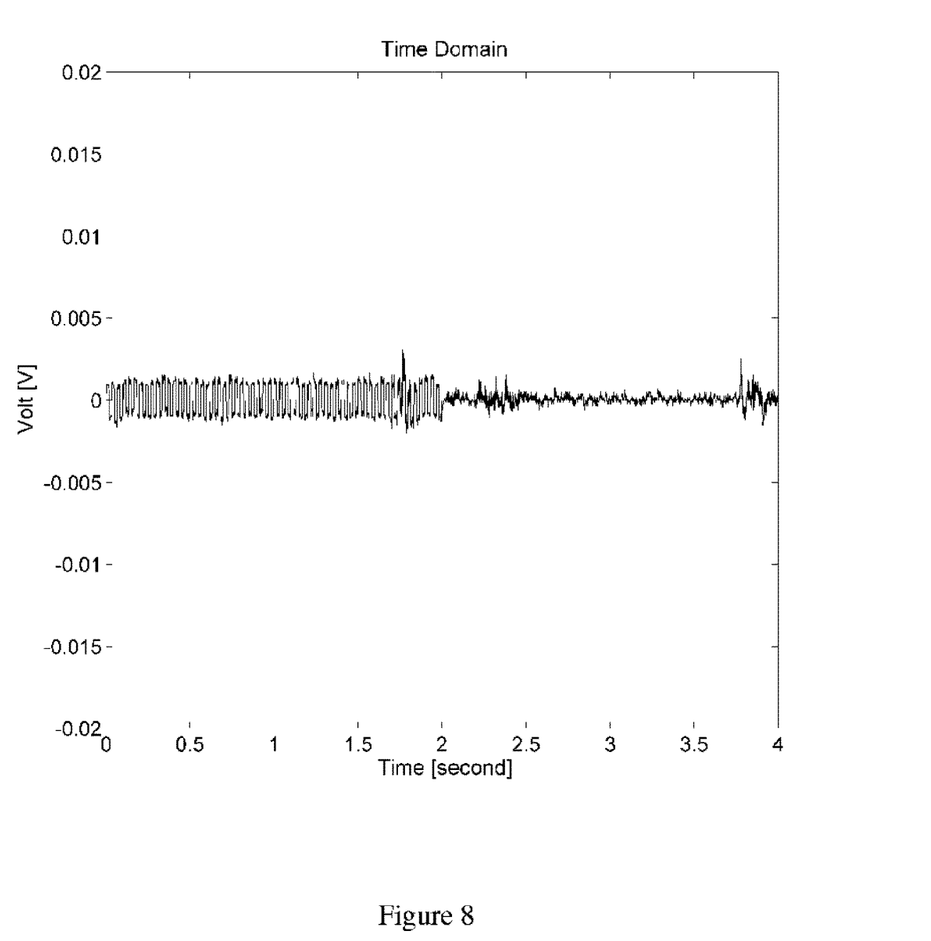
FIG. 8 illustrates a simulation of the ADC voltage when providing a test signal while no leak current is present.

FIG. 8 shows a circuit simulation of $V_{ADC}$ when there is no leak current. This is shown over two sequences, where the test generator is on for the first 2 seconds and subsequently turned off. The unit on the second axis is Volts. The EEG signal is also seen on the $V_{ADC}$ signal.

Figure 9:
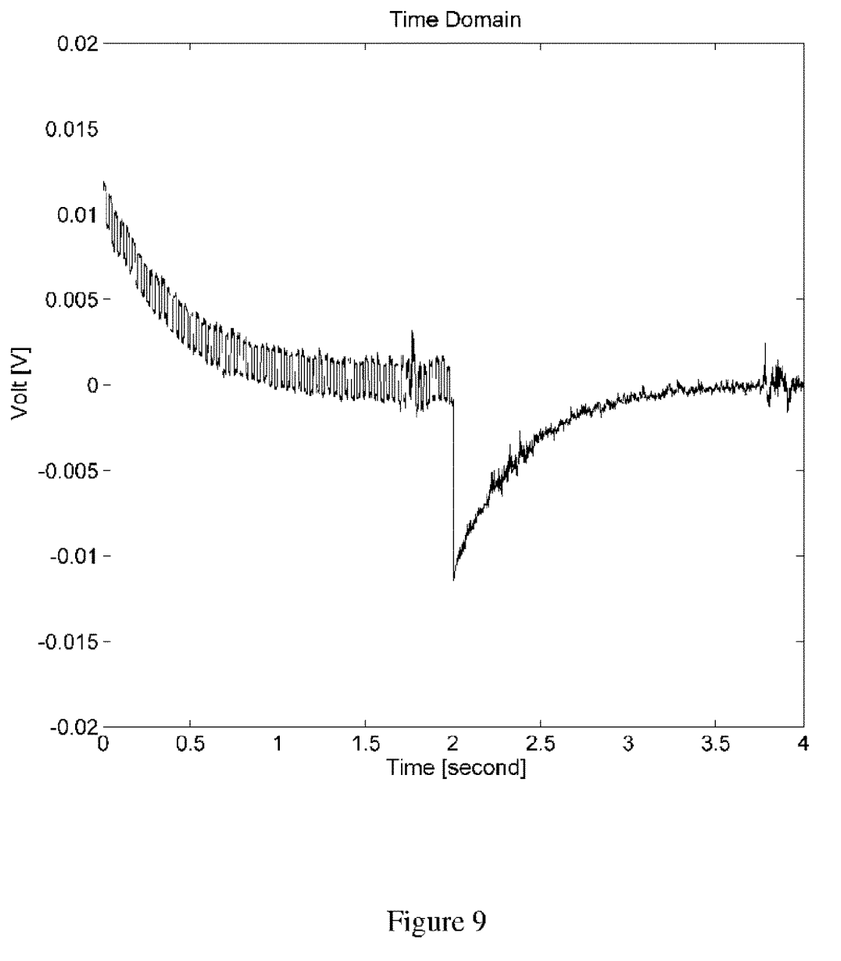
FIG. 9 illustrates a simulation of the ADC voltage when providing a test signal while a leak current is present.

FIG. 9 shows a circuit simulation of $V_{ADC}$ when there is a leak current. The difference between FIGS. 8 and 9 is the curve from the charging/discharging of the capacitor 9 caused by the leak current and the resistors 21 and 15.

In order to decide whether there is a leak current or not, and to determine the value of $I_{CL}$, an algorithm is established.

The value of α is proportional to the leakage current $I_{CL}$. A good estimate of a is found by the value of $V_{ADC}$ at t=0 and at the time where the test generator is switched off. To find $I_{CL}$ the $V_{ADC}$ value at t=0 is divided by $(R_t+R_g)$ or, alternatively, the $V_{ADC}$ value at switch off is divided by $-R_g$. These estimates can be improved by taking the average of the two, thereby reducing the variance of the estimate. If the estimate is greater than e.g. 1 µA a warning or an alarm can be given to the user, or the device can simply be turned off.

A better estimate can be found by looking at the whole progression of the test sequence since more samples are taken into account. Thereby the estimate will be less influenced by EEG or noise. Several methods exist to do this kind of estimation. One method could be taking the natural logarithm in FIG. 9 whereby a straight line is achieved. α and τ can then be determined from the slope. In practice, however, $V_{ADC}$ is not always above zero, and in order to avoid complex calculations of the logarithm due to negative numbers, the power or the absolute value of $V_{ADC}$ is calculated before calculating the logarithm. Taking the logarithm and the power of a signal is computational complex; therefore, the signal may be down-sampled by a factor of e.g. four prior to the calculation. This can be summarized in the following steps:

1. Subtract the estimated test generator signal.
2. Low-pass filter, to suppress EEG and Noise components.
3. Downsample with e.g. 4 to reduce the calculation complexity.
4. Take the power of the signal downsampled signal
5. Take the natural logarithm of the power signal. In the log domain, the tendency curve for no leak current is a horizontal line. In case of leak current the tendency curve is a line with a negative interception with the y-axis and a negative slope.
6. Fit the above signal to a straight line and find the slope. α is now the interception with the y-axis and τ is the slope of the line
7. Determine the leak current based on α. If the estimate is greater than e.g. 1 µA a warning or an alarm can be given to the user, or the device can simply be turned off.

Two α values can be determined by the above algorithm, one for start of the test generator and the other for switching it off. Each gives an estimate of $I_{CL}$. Taking the mean value of the two results in an estimate of $I_{CL}$ with lower uncertainty. However, for computational complexity reason, it is beneficial to calculate only the latter α, since it doesn't include the test generator signal.

The testing circuit further enables calculation of the impedance between the electrodes and the tissue $R_t$. This can be done by enabling a shunt resistor 18 $R_{shunt}$ on the ADC input. This shunt resistor in the circuit will change the calculation of $V_{ADC}$ to approximately:

$$V_{ADC} = V_8 \frac{R_{shunt}}{R_g + R_t + R_{shunt}}$$

where $V_g$ is the signal from test generator 8. Furthermore it is assumed that $R_{ADC}$ is much larger than $R_g$, $R_t$ and $R_{shunt}$. From this equation $R_t$ can be estimated when measuring at the frequency of the test generator, where other voltage contributions might be ignored.

We claim:

1. A personal wearable EEG monitor comprising an implantable electrode part with at least two electrodes adapted for measuring an EEG signal of a person, said electrode part comprising an electronic circuit arranged in a housing with each electrode arranged external to said housing, said electronic circuit being adapted for receiving an analogue EEG signal from said electrodes and being provided with an analogue to digital converter for converting the analogue EEG signal into a digital signal, said electrode part comprising a testing circuit for testing for faults in said electrode part, wherein said testing circuit comprises
   a capacitor coupled in serial connection to at least one of said electrodes, and
   a test signal generator for providing a test signal, said test signal generator being adapted for being coupled between said electrodes and said electronic circuit during a testing period, wherein said EEG monitor is adapted for analyzing the test signal from said signal generator for identification of faults in the electrode part.

2. The EEG monitor according to claim 1, wherein said test signal generator is arranged between said electrodes and an input of said analogue to digital converter, and wherein said EEG monitor is adapted for analyzing a signal at said input of the analogue to digital converter for identification of faults in the electrode part.

3. The EEG monitor according to claim 1, wherein an output signal from said analogue to digital converter is transferred to a digital signal processing unit arranged in the electrode part.

4. The EEG monitor according to claim 1, wherein said capacitor is coupled in serial connection to the input of said analogue to digital converter.

5. The EEG monitor according to claim 1, adapted for identifying at least one of a charging and a discharging function at an input of the analogue to digital converter and thereby detecting a current leak.

6. The EEG monitor according to claim 1, wherein a resistor is arranged across an input of the analogue to digital converter.

7. The EEG monitor according to claim 1, wherein the implantable electrode part comprises a coil for an inductive coupling to a non-implantable part, said inductive coupling being adapted for transfer of data and power.

8. The EEG monitor according to claim 1, wherein said test signal generator provides a square wave test signal with frequency between 25 and 40 Hz.

9. A method for detecting a leak current in an implanted EEG monitor according to claim 1, comprising the steps of
   providing said test signal,
   subtracting an estimate of said test signal from an output of the analogue to digital converter to obtain a resulting signal,
   low-pass filtering the resulting signal in order to suppress EEG and noise components,
   transforming the low-pass filtered signal into a logarithmic domain,
   fitting the transformed signal to a straight line,
   determining an interception with y-axis of the straight line, and
   determining if a leak current is present based at least in part on the determined interception.

10. The method according to claim 9, wherein said low-pass filtered signal is down-sampled in order to reduce the calculation complexity.

11. The method according to claim 9, wherein said step of transforming the low-pass filtered signal comprises determining the power of the low-pass filtered signal and taking the natural logarithm of the power of the low-pass filtered signal.

12. The method according to claim 9, wherein said step of transforming the low-pass filtered signal comprises determining the absolute value of the low-pass filtered signal and taking the natural logarithm of the absolute value.

13. The EEG monitor according to claim 2, wherein said capacitor is coupled in series between said at least one electrode and an input of said analog-to-digital converter, and said test signal generator is coupled to supply said test signal to another input of said analog-to-digital converter.

* * * * *